United States Patent [19]

Yoshimura et al.

[11] Patent Number: 4,497,809
[45] Date of Patent: Feb. 5, 1985

[54] CEPHALOSPORIN DERIVATIVES

[75] Inventors: Yoshinobu Yoshimura; Naoru Hamaguchi, both of Osaka; Takatsuka Yashiki, Hyogo, all of Japan

[73] Assignee: Takeda Chemical Industries, Ltd., Osaka, Japan

[21] Appl. No.: 486,820

[22] Filed: Apr. 20, 1983

[30] Foreign Application Priority Data

Apr. 30, 1982 [JP] Japan .................................. 57-73729

[51] Int. Cl.³ .................. A61K 31/545; C07D 501/56
[52] U.S. Cl. ......................................... 514/206; 544/27
[58] Field of Search ........................... 424/246; 544/27

[56] References Cited

U.S. PATENT DOCUMENTS

| | | | |
|---|---|---|---|
| 4,080,498 | 3/1978 | Numata et al. | 424/246 |
| 4,146,710 | 3/1979 | Naito et al. | 424/246 |
| 4,189,479 | 2/1980 | Kakeya et al. | 424/246 |

FOREIGN PATENT DOCUMENTS 5777690  5/1982  Japan .

Primary Examiner—Paul M. Coughlan, Jr.
Attorney, Agent, or Firm—Antonelli, Terry & Wands

[57] ABSTRACT

Cephalosporin derivatives of the formula:

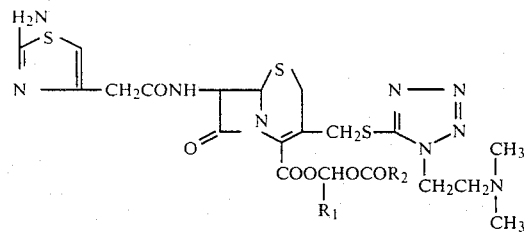

wherein $R_1$ is methyl or ethyl and $R_2$ is a straight-chain or branched alkyl group of 5 to 7 carbon atoms, and their pharmaceutically acceptable salts, which are effective as orally administrable antibiotic agents against both gram-positive- and negative-bacteria, and the production and compositions thereof, are proposed.

12 Claims, No Drawings

CEPHALOSPORIN DERIVATIVES

The present invention relates to a cephalosporin derivative of the formula:

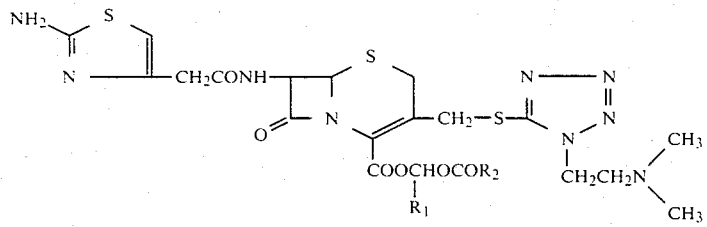

wherein $R_1$ is a hydrogen atom or a lower alkyl group having one to five carbon atoms, and $R_2$ is an alkyl group having five to thirteen carbon atoms, or its pharmaceutically acceptable salt and to a process for producing the same. It also relates to a pharmaceutical composition and an antibiotic use thereof.

It has been proposed to convert 7β-[2-(2-aminothiazol-4-yl)acetamido]-3-[[[1-(2-dimethylaminoethyl)-1H-tetrazol-5-yl]thio]methyl]ceph-3-em-4-carboxylic acid (U.S. Pat. No. 4,080,498) into its pivaloyloxymethyl ester to increase its absorption into a living body upon oral administration (U.S. Pat. No. 4,189,479).

We have extensively studied seeking a compound having excellent pharmaceutical properties, for example, good absorbability and stability and found that the above mentioned cephalosporin derivative of the formula (I) (hereinafter referred to as "Compound I") is efficiently absorbed into a living body through an intestinal tract and quickly hydrolized to free acid form thereof (non-ester form of Compound (I), which is found in the blood in a high concentration, and that Compound I is effective against gram-positive as well as gram-negative bacteria including their resistant strains and thus useful as an orally administrable antibiotic agent with a wide antibacterial spectrum. We have also found that, by conversion of Compound I into acid addition salts thereof, water-solubility, stability and absorption efficiency of Compound I are much increased and at the same time isolation and formulation of Compound I become much easier. Based on these findings, the present invention has been accomplished.

In the above mentioned formula (I), $R_1$ represents a hydrogen atom or a lower alkyl group having one to five carbon atoms which may be either a straight or branched alkyl group, for example, methyl, ethyl, propyl, butyl or pentyl. $R_2$ represents a straight or branched alkyl group having five to thirteen carbon atoms, for example, 1-ethylpropyl, 2-ethylpropyl, pentyl, 1,1-dimethylpropyl, 1,2-dimethylpropyl, 2,2-dimethylpropyl, 1-butylpropyl, 2-butylpropyl, 3-methylbutyl, 2-ethylbutyl, 1,1,2-trimethylpropyl, 1,2,2-trimethylpropyl, 2-methylbutyl, 1,1,2,2-tetramethylpropyl, 1,1-diethylpropyl, hexyl, heptyl, 1-propylbutyl, octyl, 1,1-diethyl-2-methylpropyl, nonyl, 1-butylpentyl, 1,1-diethyl-2,2-dimethylpropyl, decyl and 1-hexylheptyl. In particular, straight or branched alkyl groups having five to nine carbon atoms, for example, 1-ethylpropyl, 1,1-dimethylpropyl, 2,2-dimethylpropyl, 1-butylpropyl, 1,2,2-trimethylpropyl, 1,1-diethylpropyl, pentyl, heptyl, 3-methylbutyl, 2-methylbutyl, 1-propylbutyl, and 1-butylpentyl, are preferred. Moreover, in the case where $R_1$ is methyl or ethyl, especially preferred $R_2$ is a straight or branched alkyl group having five to seven carbon atoms such as pentyl, 2-methylbutyl, heptyl or 1-propylbutyl and in the case where $R_1$ is a hydrogen atom, especially preferred $R_2$ is a straight or branched alkyl group having nine carbon atoms such as 1-butylpentyl. The most preferred Compound I is the one wherein $R_1$ is methyl and $R_2$ is a straight or branched alkyl group having five to seven carbon atoms.

Since Compound I is basic in itself, it can be converted into acid addition salt thereof. Preferred examples of the non-toxic acids usually used for the formation of the acid addition salts of Compound I are those inorganic or organic acids which have been known in the fields of penicillins and cephalosporins to form pharmaceutically acceptable salt, for example, hydrochloric acid, sulfuric acid, phosphoric acid, maleic acid, acetic acid, citric acid, succinic acid, tartaric acid, malic acid, malonic acid, fumaric acid, benzoic acid, mandelic acid, ascorbic acid, methanesulfonic acid, etc. The aminothiazole group of Compound I may exist in the form of its tautomer, i.e. iminothiazoline.

Compound I and its salts are readily absorbed into a living body through intestinal tract and then quickly hydrolyzed at the ester linkage of the carboxyl group at the 4-position of Compound I by an intravital enzyme into the free-carboxylic acid form of Compound I (hereinafter referred to as "non-ester Compound I"). In this aspect, Compound I whose ester moiety at the 4-position is pentyl, 2-methylbutyl, heptyl, 1-propylbutyl or 1-butylpentyl is preferable.

Non-ester Compound I is remarkably superior in its antibacterial activity. That is, it shows an excellent antibacterial activity against gram-positive bacteria (e.g., *Staphylococcus aureus*), as well as gram-negative bacteria (e.g., *Escherichia coli, Klebsiella pneumonia, Proteus vulgaris, Proteus mirabilis, Proteus morganii*).

Upon oral administration, Compound I yields a high blood concentration of the non-ester of Compound I, and it is effective for the treatment of infectious diseases of human and other mammalia caused by the said bacteria, for example, respiratory or urinary infections.

Compound I of the present invention is low in toxicity ($LD_{50}$: not less than 5 g/kg, mice) and can be orally be administered. Compound I can be formulated into capsules, powders, fine granules, granules or tablets in admixture with a pharmaceutically acceptable carrier (e.g., starch, lactose, calcium carbonate, calcium phosphate), a binder (e.g., starch, gum arabic, carboxymethylcellulose, hydroxypropylcellulose, microcrystalline cellulose), a lubricant (e.g., magnesium stearate, talc) and a disintegrator (e.g., carboxymethylcellulose, talc) according to a conventional method. Alternatively, Compound I can be combined with, per mole of the Compound I, one to five molar amounts of a solid organic acid (e.g., citric acid, malic acid, tartaric acid, succinic acid, ascorbic acid, mandelic acid) and then formulated into granules, which can be brought into capsules, tablets and the like by a conventional method.

Compound I and its pharmaceutically acceptable salts are administered at a daily dose of 0.3 to 5 g per adult person, preferably 0.5 to 3 g per adult person, divided into 3 or 4 equal doses.

Compound I can be prepared by a process known per se (e.g., U.S. Pat. Nos. 4,080,498 and 4,189,479). For example, it can be prepared by reacting non-ester Compound I of the formula:

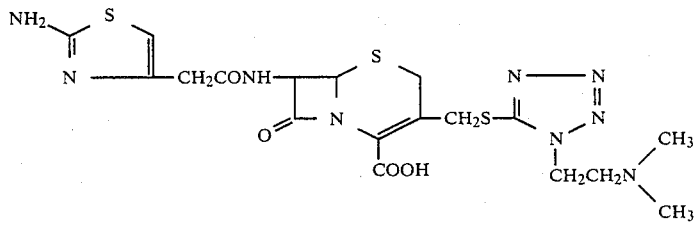

or its salt with a compound of the formula:

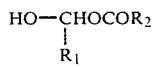

wherein $R_1$ and $R_2$ are as defined above, or its reactive derivative.

Any of the conventional reactive derivative may be used, but a compound of the formula:

wherein $R_1$ and $R_2$ are as defined above, and X is a halogen atom (e.g., chlorine, bromine or iodine) is preferable. More preferred reactive derivative is the compound of the formula (IV) wherein X is iodine, i.e., iodomethylacylate or iodoalkylacylate.

The salt of non-ester Compound I may be the acid addition salt of an inorganic acid (e.g., hydrochloric acid, sulfuric acid, nitric acid) or an organic acid (e.g., oxalic acid, p-toluenesulfonic acid) or the salt of such a base as alkali metals (e.g., sodium, potassium), alkaline earth metals (e.g., calcium, magnesium) or organic amines (e.g., triethylamine, trimethylamine, pyridine, collidine, lutidine).

This esterification reaction is usually carried out in an inert solvent. The solvent may be amides, ketones, nitriles and liquefied sulfur dioxide. More specifically, acetonitrile, N,N-dimethylformamide (hereinafter referred to as "DMF"), N,N-dimethylacetamide (hereinafter referred to as "DMAC"), hexamethylphosphorotriamide (hereinafter referred to as "HMPA"), dichloromethane, chloroform, dimethylsulfoxide (hereinafter referred to as "DMSO"), diethyl ether, dioxane, tetrahydrofuran (hereinafter referred to as "THF"), acetone, methyl ethyl ketone, and dimethoxyethane. Among these solvents, particularly preferred are DMF, DMAC, HMPA, acetone, acetonitrile and anhydrous liquefied sulfur dioxide.

The esterification reaction is usually carried out at a temperature of −20° C. to 20° C. No catalyst is required for the reaction, though a phase transfer catalyst (e.g., 18-crown-6) may be used.

In the case where anhydrous liquefied sulfur dioxide is used as a solvent, the reaction is preferably conducted at a temperature in the vicinity of the boiling point (−10° C.) of the solvent, i.e., −10° C. to −20° C. The reaction time varies depending upon the reaction conditions such as the kinds of the reactants or solvent but it is generally from about 10 minutes to 6 hours.

Alternatively, Compound I or its acid addition salts can be prepared by reacting a compound of the formula:

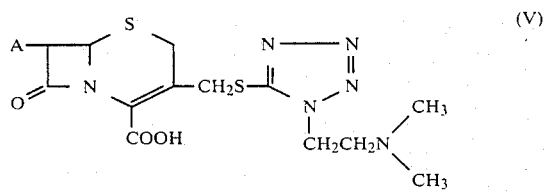

wherein A means an amino group or other acylamino group than 2-(2-aminothiazol-4-yl)acetylamino group, with the compound of the formula (IV) in substantially the same manner as that of the above mentioned esterification reaction. When the A is an acylamino group, the resulting ester is allowed to react with phosphorus pentachloride, and then with an alcohol such as methanol, ethanol, propanol, isopropanol or n-butanol [Journal of Medicinal Chemistry, Vol. 18, page 992 (1975); German (West) Patent Publication (DTOS) Nos. 2,460,331 and 2,460,332] to give a compound of the formula:

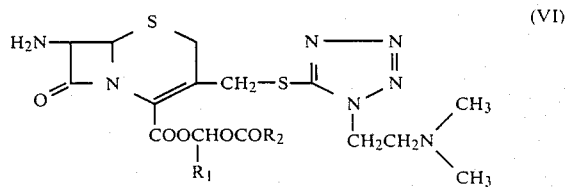

wherein $R_1$ and $R_2$ are as defined above, which is then allowed to react with 2-(2-aminothiazol-4-yl)acetic acid of the formula (VII):

to give the objective compound.

Acylamino group of the symbol A of the compound of the formula (V) may be any one known in the field of cephalosporins, but preferably acetylamino, benzoylamino, phenylacetylamino, thienylacetylamino, phenyloxyacetylamino, and 5-amino-5-carboxyl-valerylamino groups. The amino group may be protected with, for example, phthaloyl.

When the symbol A is an amino group or an acylamino group substituted with an amino group, it is preferable to protect the amino groups in reacting the compound having the amino groups. The protective group of the amino group may be any known one, for example, t-butoxycarbonyl, carboxybenzyloxy, 2-hydroxy-1-naphthocarbonyl, trichloroethoxycarbonyl, 2-ethoxycarbonyl-1-methylvinyl, and 2-methoxycarbonyl-1-methylvinyl.

Deacylation reaction of the ester prepared by the reaction of the compound (V) whose symbol A is an acylamino group with the compound (IV) is carried out according to a known method. Usually, about 2 to 5 moles of phosphorus pentachloride and about 10 to 40 moles of an alcohol are allowed to react with 1 mole of the ester. The reaction is usually carried out in an inert solvent such as halogenated hydrocarbones (e.g., dichloromethane, chloroform). A tertiary amine (e.g., triethylamine, pyridine, N,N-dimethylaniline) may be added to accelerate the reaction. The reaction temperature is in a range of $-40°$ C. to $-20°$ C., and the reaction time is usually about one hour or so.

In preparing Compound I or its acid addition salt by allowing to react the compound (VI) with the compound (VII), it is preferable that the amino group of the compound (VII) is protected with the same amino-protective group as those used for the protection of the amino group of the compound (V). In this reaction, the compound (VII) may be used in the form of its reactive derivative, for example, acid halides, acid anhydrides, mixed acid anhydrides, active amides or active esters, preferably mixed acid anhydrides and active esters. Examples of the active esters are p-nitrophenyl ester, 2,4-dinitrophenyl ester, pentachlorophenyl ester and N-hydroxyphthalimide ester. The mixed acid anhydrides are those prepared from carbonic monoesters (e.g., monomethylcarbonic acid ester, monoisobutylcarbonic acid ester) or lower ($C_{2-5}$) alkane carboxylic acid which may be substituted with a halogen atom (e.g., pivalic acid, trichloroacetic acid).

When the compound (VII) is used in the form of free acid or salt, the reaction is carried out in the presence of a suitable condensing agent. Examples of the condensing agent used in the process are N,N'-disubstituted carbodiimides (e.g., N,N'-dicyclohexylcarbodiimide), azolides (e.g., N,N'-carbonylimidazole, N,N'-thionylimidazole) and dehydrating agents (e.g., N-ethoxycarbonyl-2-ethoxy-1,2-dihydroquinoline, phosphorus oxychloride, alkoxyacetylene such as ethoxyacetylene). When the condensing agent is used, it is considered that the reaction proceeds via the formation of a reactive derivative of the used carboxylic acid derivative.

The reaction is usually carried out smoothly in a solvent. Any conventional solvent such as water, acetone, diisobutyl ketone, THF, ethyl acetate, dioxane, acetonitrile, chloroform, dichloromethane, dichloroethylene, pyridine, dimethylaniline, DMF, DMAC, DMSO and a mixture thereof can be used as far as it does not make any harm to the reaction. The reaction is usually conducted at the room temperature or under cooling, though the reaction temperature is not particularly limited. In the case where the reaction proceeds with removal of an acid, a basic substance may be added to the reaction system as needed. As the basic substance, aliphatic, aromatic or alicyclic nitrogen-bases or alkaline earth metal carbonates or hydrogencarbonates, for example, triethylamine, N,N-dimethylaniline, N-ethylmorpholine, pyridine, collidine, 2,6-lutidine, sodium carbonate, potassium carbonate, potassium hydrogencarbonate, or sodium hydrogencarbonate are often used. In the case where the acylation reaction proceeds dehydratingly, it is preferable to eliminate water from the solvent, or the reaction operation is carried out in an atmosphere of an inert gas such as nitrogen gas to avoid humidity. When the reaction product has a protective group, the protective group can be removed by a known method.

Compound I and its acid addition salt can also be prepared by reacting the compound (VI) with a 4-halogeno-3-oxobutyryl halide, which is prepared by reacting diketene with an equimolar amount of a halogen (e.g., chlorine, bromine, iodine), to give a compound of the formula:

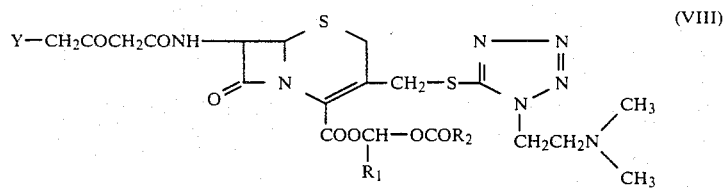

(VIII)

wherein Y is a halogen atom (e.g., chlorine, bromine, iodine), and $R_1$ and $R_2$ are as defined above, and reacting the compound (VIII) thus prepared with thiourea.

In the reaction of the compound (VIII) with thiourea, thiourea may be used as it is or in the form of salt such as alkali metal salt (e.g., lithium, sodium, potassium) or ammonium salt. The reaction is usually carried out by mixing equimolar amounts of the reactants in a solvent. If necessary, it can be conducted in the presence of 1 or 2 equimolar amounts of a base. The solvent suitable for this reaction is for example, water, methanol, ethanol, acetone, dioxane, acetonitrile, chloroform, ethylene chloride, THF, ethyl acetate, DMF, DMAC or DMSO. Among these solvents, a hydrophilic solvent may be used in combination with water. The base above is alkali metal hydroxides such as sodium hydroxide or potassium hydroxide, alkali metal carbonates such as sodium carbonate or potassium carbonate, alkali metal hydrogencarbonates such as sodium hydrogencarbonate or organic tertiary amines such as triethylamine, trimethylamine or pyridine. The reaction temperature is not particularly limited, but the reaction is preferably carried out under cooling. Generally, the reaction proceeds smoothly and it is usually completed within 10 minutes. However, in certain cases, more than 30 minutes is needed to complete the reaction.

The compound (VIII) can readily be prepared by the above mentioned method. It can also be prepared by some other known processes. Furthermore, the compound I or its acid addition salt is prepared by the following steps: (1) A compound of the formula

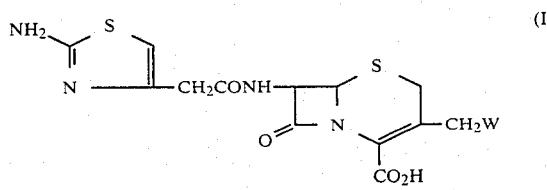

(wherein W is an acetoxy or an acetoacetoxy group), is allowed to react with a compound (IV) under similar conditions of esterification to those described above, thereby to produce a compound of the formula (X) below

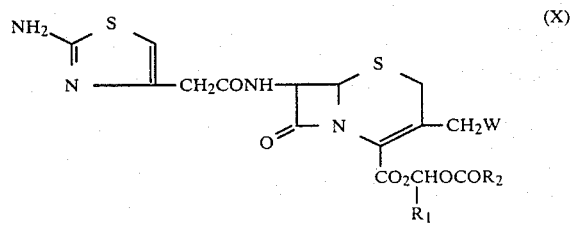

(wherein W is the same as above), and (2) then the compound (X) is allowed to react with 1-(2-dimethylaminoethyl)-5-mercapto-1H-tetrazole. In the reaction (2), almost equimolar amount of both compounds is suitable. These reactions can be smoothly carried out in a solvent, for instance, water, acetone, THF, ethyl acetate, dioxane, acetonitrile, chloroform, dichloromethane, DMF, DMAC or DMSO. In the case of water, another water miscible solvent is recommended to admix. Presence of an inorganic base in the reaction system is preferable. Examples of the base are alkali or alkaline earth metal carbonate or bicarbonate, e.g. sodium carbonate, potassium carbonate, sodium bicarbonate or potassium bicarbonate. Amount of the base present in the reaction system is about equimoles to a coreactant of the compound (X). The reaction temperature range is not particularly limited, but normally room temperature to 40° C., or to 60° C., and the reaction time is roughly from 30 minutes to 3 hours, depending on kinds of solvents and temperature.

If the Compound I or its salt prepared as above contains its Δ²-isomer, the isomer can be converted to Compound I or its salt by, for example, isomerizing the isomer to the Δ³-isomer by a known method [Journal of Medicinal Chemistry, Vol. 18, 986 (1975)], or converting the isomer to the Δ³-isomer via a corresponding S-oxide derivative and reducing it.

If the Compound I thus obtained is in the form of a free base, it can be converted to an acid addition salt thereof by dissolving it in an inert solvent (e.g., dichloromethane, chloroform) and adding 1 to 10 mole per 1 mole of Compound I of an acid to the solvent. In case where Compound I or an acid addition salt thereof thus obtained is a racemic mixture, the optically active isomers (D-isomer, L-isomer) can be isolated by the optical resolution according to known procedures.

Compound I or its acid addition salt thus obtained may further be purified by known methods, for example, extraction with solvent, adjustment of pH, solvent-transformation, crystallization, recrystallization or chromatography.

The compound of the formula (IV), which is used as the starting material for the production of Compound I or its salt, can be prepared by the process shown below:

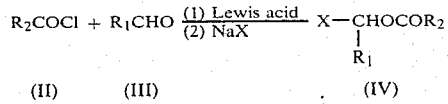

wherein $R_1$, $R_2$ and X have the same meanings as above.

For instance, the compound of the formula (IV) wherein X is iodine, i.e., iodomethyl acylate or iodoalkyl acylate can be prepared by reacting an acid chloride (II) with an aldehyde (III) (e.g., paraformaldehyde, paraldehyde or acetaldehyde) in the presence of a Lewis acid followed by sodium iodide. The first step of this reaction is conducted in the presence of such a Lewis acid as anhydrous zinc chloride, aluminum chloride or stannic chloride. This reaction proceeds by either cooling to −40° to 30° C., preferably −40° to 0° C. or heating to 30° to 140° C., preferably 90° to 140° C. The reaction time varies with the reaction temperature, but one to three hours under cooling or one to six hours under heating is usually needed. The reaction sufficiently proceeds even in the absence of a solvent.

After the first step reaction has been completed, the chloromethyl acylate or chloroalkyl acylate can be obtained by distilling or column chromatographing the reaction mixture. Chloromethyl acylate or chloroalkyl acylate thus obtained is allowed to react with sodium iodide to give the objective iodomethyl acylate or iodoalkyl acylate (The second step reaction). The second step reaction is carried out in the presence of a general solvent such as acetone, acetonitrile, DMF, DMSO and the like. The reaction temperature may be room temperature or about 40° to 50° C. The reaction time is 15 minutes to 6 hours, preferably 15 minutes to 2 hours.

The product can be isolated and purified with known techniques such as extraction with a solvent, adjustment of pH, solvent-transformation, crystallization, recrystallization or chromatography.

The following examples are given to illustrate the present invention more precisely. However, they are not intended to limit the present invention.

In the examples, the used symbols have the following meanings:
s: singlet
b-s: broad singlet
d: doublet
d,d: doublet doublet
t: triplet
q: quartet
Ab-q: AB-type quartet
m: multiplet
b.p.: boiling point Preparation of starting materials Preparation 1

Iodomethyl 2-n-butyl hexanoate:
(1) A mixture of 30 g of 2-n-butyl hexanoyl chloride, 4.5 g of paraformaldehyde and catalytic amount of anhydrous zinc chloride was heated at 120°–140° C. for 2 hours. The reaction mixture was then distilled under a reduced pressure and the fraction of b.p. 72°–96° C./6 mmHg was again distilled to give 18 g of chloromethyl 2-n-butylhexanoate, b.p. 88°–90° C./6.5 mmHg.

IR ν (liquid film)cm$^{-1}$: 1770, 1750, 710.

NMR(CDCl$_3$)δ: 0.88(t, J=6 Hz, 6H), 1.00–1.90(m, 12H), 2.22–2.60(m, 1H), 5.72(s, 2H).

(2) In 100 ml of acetonitrile warmed to 40° C., 18 g of sodium iodide was dissolved.

To this solution, 8 g of the chloromethyl 2-n-butylhexanoate prepared as above (1) was added and the mixture was stirred for 30 minutes.

After the removal of solid portion by filtration, the reaction mixture was evaporated under reduced pressure. A mixture of petroleum ether and a 5% aqueous solution of sodium thiosulfate was added to the residue. The petroleum ether layer was separated and washed with a 5% aqueous solution of sodium thiosulfate. It was dried over anhydrous magnesium sulfate and evaporated under a reduced pressure to give 6.2 g of the the captioned compound.

IR(liquid film)cm$^{-1}$: 1760, 1755.

Preparation 2

Iodomethyl 2-n-hexyloctanoate:

(1) Chloromethyl 2-n-hexyloctanoate was prepared in the same manner as that of the above Preparation 1, (1).

IR(liquid film)cm$^{-1}$: 1765, 720.

(2) Iodomethyl 2-n-hexyloctanoate was prepared by reacting chloromethyl 2-n-hexyloctanoate in the same way as that of Preparation 1, (2).

IR(liquid film)cm$^{-1}$: 1760.

Preparation 3

1-Iodoethyl n-valerate:

(1) A mixture of 25 g of n-valeryl chloride, 9 g of paraldehyde and a catalytic amount of anhydrous zinc chloride was stirred at 130°–140° C. for 4 hours. The mixture was distilled under reduced pressure and the fraction distilled at b.p. 64°–80° C./32 mmHg was again distilled to yield 18 g of 1-chloroethyl n-valerate, b.p. 76°–80° C./27 mmHg.

IR(liquid film)cm$^{-1}$: 1760, 670.

NMR(CDCl$_3$)δ: 0.91(t, J=7 Hz, 3H), 1.1–1.9(m, 4H), 1.77(d, J=6 Hz, 3H), 2.34(t, J=7 Hz, 2H), 6.59(q, J=6 Hz, 1H).

Elementary analysis: as C$_7$H$_{13}$ClO$_2$: Calcd: C, 51.07; H, 7.96%, Found: C, 51.15; H, 8.03%.

(2) Using the 1-chloroethyl n-valerate prepared as above (1), 1-iodoethyl n-valerate was prepared in the same manner as that of Preparation 1, (2).

IR(liquid film)cm$^{-1}$: 1755.

Preparation 4

1-Iodoethyl isovalerate:

(1) 1-Chloroethyl isovalerate was prepared in the same manner as that of Preparation 3, (1).

IR(liquid film)cm$^{-1}$: 1760, 660.

(2) 1-Iodoethyl isovalerate was prepared by reacting the 1-chloroethyl isovalerate prepared as above in the same manner as that of Preparation 1, (1).

IR(liquid film)cm$^{-1}$: 1760.

Preparation 5

1-Iodoethyl hexanoate:

(1) 1-Chloroethyl hexanoate was prepared in the same manner as that of Preparation 3, (1).

IR(liquid film)cm$^{-1}$: 1760, 670.

NMR(CDCl$_3$)δ: 0.83(t, J=7 Hz, 3H), 1.1–1.5(m, 4H), 1.77(d, J=6 Hz, 3H), 6.56(q, J=6 Hz, 1H).

Elementary analysis: as C$_8$H$_{15}$ClO$_2$: Calcd: C, 53.78, H, 8.46%, Found: C, 54.00; H, 8.35%.

(2) The compound prepared in the above (1) was allowed to react in the same manner as that of Preparation 1, (2) to give 1-iodoethylhexanoate.

IR(liquid film)cm$^{-1}$: 1755.

Preparation 6

1-Iodoethyl 4-methylvalerate:

(1) 1-Chloroethyl 4-methylvalerate was prepared in the same manner as that of Preparation 3, (1).

IR(liquid film)cm$^{-1}$: 1765, 660.

NMR(CDCl$_3$)δ: 0.91(d, J=6 Hz, 6H), 1.3–1.88(m, 3H), 1.78(d, J=6 Hz, 3H), 2.34(t, J=7 Hz, 2H), 6.57(q, J=6 Hz, 1H).

(2) 1-Iodoethyl 4-methylvalerate was prepared by reacting the 1-chloroethyl 4-methylvalerate prepared as above in the same manner as that of Preparation 1, (2).

IR(liquid film)cm$^{-1}$: 1755.

Preparation 7

1-Iodoethyl 3-methylvalerate:

(1) 1-Chloroethyl 3-methylvalerate was prepared in the same manner as that of Preparation 3, (1).

IR(liquid film)cm$^{-1}$: 1765, 1750, 660.

(2) 1-Iodoethyl 3-methylvalerate was prepared by reacting the 1-chloroethyl 3-methylvalerate prepared as above in the same manner as that of Preparation 1, (2).

IR(liquid film)cm$^{-1}$: 1760.

Preparation 8

1-Iodoethyl heptanoate:

(1) 1-Chloroethyl heptanoate:

A mixture of 25 g of n-heptanoyl chloride and a catalytic amount of anhydrous zinc chloride was cooled to −40° C., and 10 ml of acetaldehyde was added dropwise to the mixture with stirring. The reaction mixture was then allowed to warm up to room temperature in the course of 2 hours. The mixture was subjected to the column chromatography on silica gel (70–230 mesh. 100 ml) with 300 ml of petroleum ether as eluent. The eluate was evaporated under reduced pressure to give 28 g of 1-chloroethyl heptanoate.

IR(liquid film)cm$^{-1}$: 1760, 660.

(2) The 1-chloroethyl n-heptanoate prepared as above was reacted in the same manner as that of Preparation 1, (2) to give 1-iodoethyl n-heptanoate.

IR(liquid film)cm$^{-1}$: 1755.

Preparation 9

1-Iodoethyl n-octanoate:

(1) 1-Chloroethyl n-octanoate was prepared in the same manner as that of Preparation 8, (1).

IR(liquid film)cm$^{-1}$: 1755, 660.

(2) The 1-chloroethyl n-octanoate prepared as above was reacted in the same manner as that of Preparation 1, (2) to give 1-iodoethyl n-octanoate.

IR(liquid film)cm$^{-1}$: 1755.

Preparation 10

1-Iodoethyl 2-n-propylvalerate:

(1) 1-Chloroethyl 2-n-propylvalerate was prepared in the same manner as that of Preparation 8, (1).

IR(liquid film)cm$^{-1}$: 1760, 660.

(2) The 1-chloroethyl 2-n-propylvalerate prepared as above was allowed to react in the same manner as that of Preparation 1, (1) to give 1-iodoethyl 2-n-propylvalerate.
IR(liquid film)cm$^{-1}$: 1760.

Preparation 11

1-Iodoethyl n-decanoate:

(1) 1-Chloroethyl n-decanoate was prepared in the same manner as of Preparation 8, (1).
IR(liquid film)cm$^{-1}$: 1760, 660.

(2) The 1-chloroethyl n-decanoate prepared as above was allowed to react in the same manner as that of Preparation 1, (2) to give 1-iodoethyl n-decanoate.
IR(liquid film)cm$^{-1}$: 1760.

Preparation 12

1-Iodopropyl n-hexanoate:

(1) 1-Chloropropyl n-hexanoate was prepared in the same manner as that of Preparation 8, (1).
IR(liquid film)cm$^{-1}$: 1750.

(2) The 1-chloropropyl n-hexanoate was allowed to react in the same manner as that of Preparation 1, (2) to give 1-iodopropyl n-hexanoate.
IR(liquid film)cm$^{-1}$: 1755.

Preparation 13

1-Iodoethyl pivalate:

(1) 1-Chloroethyl pivalate was prepared in the same manner as that of Preparation 8, (1).
IR(liquid film)cm$^{-1}$: 1755, 660.

(2) The 1-chloroethyl pivalate was allowed to react in the same manner as that of Preparation 1, (2) to give 1-iodoethyl pivalate.
IR(liquid film)cm$^{-1}$: 1755.

Preparation 14

1-Iodoethyl isobutyrate:

(1) 1-Chloroethyl isobutyrate was prepared in the same manner as that of Preparation 8, (1).
IR(liquid film)cm$^{-1}$: 1760, 660.

(2) The 1-chloroethyl isobutyrate prepared as above was allowed to react in the same manner as that of Preparation 1, (1) to give 1-iodoethyl isobutyrate.
IR(liquid film)cm$^{-1}$: 1755.

Preparation 15

1-Iodoethyl 2-ethylbutyrate:

(1) In the same manner as Preparation 8, (1), 1-chloroethyl 2-ethylbutyrate was prepared, b.p. 83°–85° C./35 mmHg.
IR(liquid film)cm$^{-1}$: 1760, 670.

(2) The compound prepared as above (1) was treated in the same manner as in preparation 1, (2) to give 1-iodoethyl 2-ethylbutyrate.
IR(liquid film)cm$^{-1}$: 1755.

Preparation 16

1-Iodoethyl 3-ethylvalerate:

(1) In the same manner as of Preparation 8, (1), 1-chloroethyl 3-ethylvalerate was prepared.
b.p. 100°–102° C./45 mmHg
IR(liquid film)cm$^{-1}$: 1760, 670.
NMR(CDCl$_3$)δ: 0.87(t, J=6 Hz, 6H, CH$_3\times$2), 1.1–1.6 (m, 4H, CH$_2\times$2), 1.77(d, J=6 Hz, 3H, C$\underline{H}_3$CH), 2.88(d, J=6 Hz, 2H, C$\underline{H}_2$CO), 6.55(q, J=6 Hz, 1H, OCHCH$_3$).
Elemental analysis: as C$_9$H$_{17}$O$_2$Cl: Calcd: C, 56.10; H, 8.89%, Found: C, 56.17; H, 9.04%.

(2) The 1-chloroethyl 3-ethylvalerate prepared as above was treated in the same manner as that of Preparation 1, (2) to give 1-iodoethyl 3-ethylvalerate.
IR(liquid film)cm$^{-1}$: 1760.

EXAMPLE 1

Preparation of 1-(pivaloyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate:

In 50 ml of dimethylformamide, 5.0 g of sodium 7β-[2-(2-aminothiazol-4-yl)acetamido]-3-[[[1-(2-dimethylaminoethyl)-1H-tetrazol-5-yl]thio]methyl]ceph-3-em-4-carboxylate was dissolved. After the mixture was cooled to −5° C., 4 g of 1-iodoethyl pivalate was added to it at one time with stirring and the mixture was stirred for 10 minutes. The reaction mixture was poured into a mixture of 300 ml of ethyl acetate and 200 ml of ice water, and the organic layer was separated. The aqueous layer was extracted with 200 ml of ethyl acetate and then the combined organic layer was washed with 150 ml of ice-water for three times and then with a saturated aqueous solution of sodium chloride for three times. The extract was dried over anhydrous magnesium sulfate and evaporated under reduced pressure.

Isopropyl ether was added to the residue and the resulted powders were collected by filtration, washed with isopropyl ether and dried to yield 1.6 g of the captioned compound.

IR(Nujol)cm$^{-1}$: 1775, 1755, 1740, 1640.
NMR(d$_6$-DMSO)δ: 1.12(s, 9H), 1.47 and 1.51(two ds, J=6 Hz, 3H), 2.17(s, 6H), 2.70(t, J=6 Hz, 2H), 3.36(s, 2H), 3.58 and 3.84(ABq, J=18 Hz, 2H), 4.00 and 4.16(ABq, J=13.5 Hz, 2H), 4.37(t, J=6 Hz, 2H), 5.06 and 5.10(two ds, J=4.5 Hz, 1H), 5.72(dd, J=4.5 Hz, J=9.0 Hz, 1H), 6.22(s, 1H), 6.8–7.1(m, 3H), 8.87(d, J=9 Hz, 1H)

Elemental analysis: as C$_{25}$H$_{35}$N$_9$O$_6$S$_3$: Calcd: C, 45.93; H, 5.40; N, 19.28%, Found: C, 45.62; H, 5.20; N, 18.97%.

EXAMPLE 2

Preparation of 1-(pivaloyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate. dihydrochloride:

In 25 ml of ethylacetate, 0.5 g of the compound prepared in Example 1 was dissolved and etheral hydrogen chloride was added to the solution. The precipitated powdery product was collected by filtration, washed with ether and dried to give 0.35 g of the captioned compound.

IR(Nujol)cm$^{-1}$: 1785, 1755, 1675.
NMR(D$_2$O)δ: 1.50(s, 9H), 1.84(d, J=6 Hz, 3H), 3.37 (s, 6H), 4.02–4.30(m, 2H), 4.32(s, 2H), 4.51(t, J=6 Hz, 2H), 4.51 and 4.73(ABq, J=18 Hz, 2H), 5.26 (t, J=6 Hz, 2H), 5.50(d, J=4.5 Hz, 1H), 5.99(d, J=4.5 Hz, 1H), 7.00(s, 1H), 7.21(q, J=6 Hz, 1H).

Elemental analysis: as C$_{25}$H$_{35}$N$_9$O$_6$S$_3$.2HCl.2.5H$_2$O: Calcd: C, 38.90; H, 5.50; N, 16.34%, Found: C, 39.24; H, 5.78; N, 16.00%.

EXAMPLE 3

Preparation of 1-(isobutyryloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate:

The above captioned compound was prepared in substantially the same manner as that of Example 1, using 1-iodoethyl isobutyrate.

IR(KBr)cm$^{-1}$: 1780, 1750, 1660, 1650.

NMR(d$_6$-DMSO)δ: 0.90(d, J=6 Hz, 6H), 1.48 and 1.51 (two ds, J=6 Hz, 3H), 2.24(s, 6H), 2.76(t, J=6 Hz, 2H), 3.37(s, 2H), 3.76(b-s, 2H), 4.17 and 4.27 (ABq, J=13.5 Hz, 2H), 4.42(t, J=6 Hz, 2H), 5.0-5.2 (m, 1H, C$_6$-H), 5.6-5.9(m, 1H, C$_7$-H), 6.23(s, 1H), 6.72-7.18(m, 3H), 8.86(d, J=9 Hz, 1H).

Elemental analysis: as C$_{24}$H$_{33}$N$_9$O$_6$S$_3$: Calcd: C, 45.06; H, 5.20; N, 19.71%, Found: C, 44.96; H, 5.49; N, 19.72%.

EXAMPLE 4

Preparation of 1-(n-valeryloxy)ethyl 7β-[2-(2-aminothiazol-4-yl)acetamido]-3-[[[1-(2-dimethylaminoethyl)-1H-tetrazol-5-yl]thio]-methyl]ceph-3-em-4-carboxylate:

The above captioned compound was prepared in the same manner as that of Example 1, using 1-iodoethyl n-valerate.

IR(Nujol)cm$^{-1}$: 1780, 1750, 1715, 1665, 1635.

NMR(d$_6$-DMSO)δ: 0.87(t, J=7 Hz, 3H), 1.1-1.7(m, 7H), 2.18(s, 6H), 2.36(t, J=7 Hz, 2H), 2.69(t, J=6 Hz, 2H), 3.37(s, 2H), 3.73(b-s, 2H), 4.13-4.40(ABq, J=13.5 Hz, 2H), 4.37(t, J=6 Hz, 2H), 5.0-5.2(m, 1H), 5.6-5.9(m, 1H), 6.23(s, 1H), 6.55-7.15(m, 3H), 8.85(d, J=9 Hz, 1H).

Elemental analysis: as C$_{25}$H$_{35}$N$_9$O$_6$S$_3$: Calcd: C, 45.93; H, 5.40; N, 19.28%, Found: C, 45.66; H, 5.45; N, 19.16%.

EXAMPLE 5

Preparation of 1-(isovaleryloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate:

The above mentioned objective compound was prepared in the same manner as that of Example 1, using 1-iodoethyl isovalerate.

IR(Nujol)cm$^{-1}$: 1775, 1750, 1670.

NMR(d$_6$-DMSO)δ: 0.92(d, J=6 Hz, 6H), 1.49 and 1.54 (two ds, J=6 Hz, 3H), 2.27(s, 6H), 2.28(t, J=6 Hz, 2H), 2.80(t, J=6 Hz, 2H), 3.37(s, 2H), 3.73(b-s, 2H), 4.17 and 4.31(ABq, J=13.5 Hz, 2H), 4.43(t, J=6 Hz, 2H), 5.00-5.20(m, 1H), 5.58-5.92(m, 1H), 6.23(s, 1H), 6.68-7.18(m, 3H), 8.86(d, J=9 Hz, 1H).

Elemental analysis: as C$_{25}$H$_{35}$N$_9$O$_6$S$_3$.½H$_2$O: Calcd: C, 45.30; H, 5.47; H, 19.01%, Found: C, 45.58; H, 5.65; N, 18.41%.

EXAMPLE 6

Preparation of 1-(n-hexanoyloxy)ethyl 7β-[2-(2-aminoethiazol-4-yl)acetamido]-3-[[[1-(2-dimethylaminoethyl)-1H-tetrazol-5-yl]thio]methyl]ceph-3-em-4-carboxylate:

In 50 ml of dimethylformamide, 5.0 g of sodium 7β-[2-(2-aminothiazol-4-yl)acetamido]-3-[[[1-(2-dimethylaminoethyl)-1H-tetrazol-5-yl]thio]methyl]ceph-3-em-4-carboxylate was dissolved. After the mixture was cooled to −5° C., 5 g of 1-iodoethyl n-hexanoate was added at once with stirring. The mixture was stirred for another 10 minutes and poured into a mixture of 300 ml of ethyl acetate and 200 ml of ice-water. The organic layer was isolated, and the aqueous layer was extracted with 200 ml of ethyl acetate. The combined organic layer was washed with 150 ml of ice-water for three times and with a saturated aqueous solution of sodium chloride for three times. The solvent was dried over anhydrous magnesium sulfate and evaporated under reduced pressure. Isopropyl ether was added to the residue and the precipitated powdery product was collected by filtration and dried to give 1.8 g of the objective compound.

IR(Nujol)cm$^{-1}$: 1780, 1750, 1670, 1640.

NMR(d$_6$-DMSO)δ: 0.84(t, J=6 Hz, 3H), 1.1-1.8(m, 9H), 2.17(s, 6H), 2.26(t, J=6 Hz, 2H), 2.69(t, J=6 Hz, 2H), 3.37(s, 2H), 3.58 and 3.81(ABq, J=18 Hz, 2H), 4.17 and 4.33(ABq, J=13.5 Hz, 2H), 4.37(t, J=6 Hz, 2H), 5.00-5.15(m, 1H), 5.55-5.86(m, 1H), 6.23(s, 1H), 6.65-7.15(m, 3H), 8.84(d, J=9 Hz, 1H).

Elemental analysis: as C$_{26}$H$_{37}$N$_9$O$_6$S$_3$: Calcd: C, 46.76; H, 5.58; N, 18.88%, Found: C, 46.58; H, 5.43; N, 18.49%.

EXAMPLE 7

Preparation of 1-(n-hexanoyloxy)ethyl 7β-[2-(2-aminotriazol-4-yl)acetamido]-3-[[[1-(2-dimethylaminoethyl)-1H-tetrazol-5-yl]thio]methyl]ceph-3-em-4-carboxylate.dihydrochloride:

In 25 ml of ethyl acetate, 0.5 g of the compound prepared in Example 6 was dissolved, and etheral hydrogen chloride was added to the solution. The resulting precipitates were collected by filtration, washed with ether and dried to give 0.37 g of the objective compound.

IR(Nujol)cm$^{-1}$: 1780, 1750, 1680.

NMR(D$_2$O)δ: 1.30-2.10(m, 12H), 2.70(t, J=6 Hz, 2H), 3.38(s, 6H), 4.12 and 4.33(ABq, J=16 Hz, 2H), 4.13 (s, 2H), 4.20(t, J=6 Hz, 2H), 4.63(b-s, 2H), 5.32 (t, J=6 Hz, 2H), 5.45(d, J=4.5 Hz, 1H), 5.99(d, J=4.5 Hz, 1H), 7.02(s, 1H), 7.23(q, J=6 Hz, 1H).

Elemental analysis: as C$_{26}$H$_{37}$N$_9$O$_6$S$_3$.2HCl.2H$_2$O: Calcd: C, 40.25; H, 5.60; N, 16.25%, Found: C, 40.14; H, 6.02; N, 15.99%.

EXAMPLE 8

Preparation of 1-(4-methylpentanoyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate:

The above mentioned compound was prepared in the same manner as that of Example 6, using 1-iodoethyl 4-methylvalerate.

IR(Nujol)cm$^{-1}$: 1785, 1750, 1710, 1670, 1640.

NMR(d$_6$-DMSO)δ: 0.83(d, J=6 Hz, 6H), 1.2-1.75(m, 6H), 2.18(s, 6H), 2.26(t, J=6 Hz, 2H), 2.68(t, J=6 Hz, 2H), 3.37(s, 2H), 3.59 and 3.83(ABq, J=18.0 Hz, 2H), 4.14 and 4.33(ABq, J=13.5 Hz, 2H), 4.37(t, J=6 Hz, 2H), 5.0-5.2(m, 1H), 5.58-5.88 (m, 1H), 6.23(s, 1H), 6.68-7.17(m, 3H), 8.84(d, J=9 Hz, 1H).

Elemental analysis: as C$_{26}$H$_{37}$N$_9$O$_6$S$_3$: Calcd: C, 46.76; H, 5.58; N, 18.88%, Found: C, 46.46; H, 5.47; N, 18.75%.

EXAMPLE 9

Preparation of 1-(4-methylpentanoyloxy)ethyl 7β-[2-(2-aminothiazol-4-yl)acetamido]-3-[[[1-(2-dimethylaminoethyl)-1H-tetrazol-5-yl]-thio]methyl]ceph-3-em-4-carboxylate.dihydrochloride:

The above mentioned compound was prepared by treating 0.5 g of the compound prepared in Example 8 in the the same manner as in Example 7.

IR(Nujol)cm$^{-1}$: 1785, 1755, 1675.

NMR(D$_2$O)δ: 1.17(d, J=6 Hz, 6H), 1.30-1.97(m, 4H), 1.82(d, J=6 Hz, 3H), 2.76(t, J=6 Hz, 2H), 3.37(s, 6H), 4.11(s, 2H), 4.29 and 4.68(ABq, J=18 Hz, 2H), 5.23(t, J=6 Hz, 2H), 5.41(d, J=4.5 Hz, 1H), 5.98(d, J=4.5 Hz, 1H), 7.01(s, 1H), 7.23(q, J=6 Hz, 1H)

Elemental analysis: as $C_{26}H_{37}N_9O_6S_3.2HCl.2.5H_2O$: Calcd: C, 39.79; H, 5.66; N, 16.07%, Found: C, 39.84; H, 5.53; N, 15.73%.

EXAMPLE 10

Preparation of 1-(3-methylpentanoyloxy)ethyl 7β-[2-(2-aminothiazol-4-yl)acetamido]-3-[[[1-(2-dimethylaminoethyl)-1H-tetrazol-5-yl]-thio]methyl]ceph-3-em-4-carboxylate:

The above mentioned compound was prepared in the same manner as in Example 6, using 1-iodoethyl 3-methylvalerate.

IR(Nujol)cm$^{-1}$: 1780, 1750, 1710, 1670, 1640.

NMR(d$_6$-DMSO)δ: 0.81(t, J=6 Hz, 3H), 0.87(d, J=6 Hz, 3H), 1.0–1.4(m, 2H), 1.47–1.51(two ds, J=6 Hz, 3H), 1.65–1.95(m, 1H), 2.17(s, 6H), 2.23(t, J=6 Hz, 2H), 2.67(t, J=6 Hz, 2H), 3.37(s, 2H), 3.57 and 3.84(ABq, J=18 Hz, 2H), 4.14 and 4.36(ABq, J=13.5 Hz, 2H), 4.37(t, J=6 Hz, 2H), 5.00–5.17(m, 1H), 5.6–5.9(m, 1H), 6.23(s, 1H), 6.68–7.12(m, 3H), 8.85(d, J=9 Hz, 1H).

Elemental analysis: as $C_{26}H_{37}N_9O_6S_3$: Calcd: C, 46.76; H, 5.58; N, 18.88%, Found: C, 46.65; H, 5.46, N, 18.96%.

EXAMPLE 11

Preparation of 1-(3-methylpentanoyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate.dihydrochloride:

The above mentioned compound was prepared by treating the compound prepared in Example 10 in the same manner as that of Example 7.

IR(Nujol)cm$^{-1}$: 1785, 1780, 1680.

NMR(d$_6$-DMSO)δ: 1.17(t, J=6 Hz, 3H), 1.20(d, J=6 Hz, 3H), 1.85(d, J=6 Hz, 3H), 1.97–2.41(m, 1H), 2.58(t, J=6 Hz, 2H), 3.38(s, 6H), 4.12(b-s, 2H), 4.70(b-s, 2H), 5.24(t, J=6 Hz, 2H), 5.47(d, J=4.5 Hz, 1H), 5.98(d, J=4.5 Hz, 1H), 7.02(s, 1H), 7.21 (q, J=6.0 Hz, 1H).

Elemental analysis: as $C_{26}H_{37}N_9O_6S_3.2HCl.2H_2O$: Calcd: C, 40.25; H, 5.60; N, 16.25%, Found: C, 40.31; H, 5.54; N, 16.02%.

EXAMPLE 12

Preparation of 1-(n-heptanoyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate:

The above mentioned compound was prepared in the same manner as that of Example 6, using 1-iodoethyl heptanoate.

IR(Nujol)cm$^{-1}$: 1780, 1750, 1715, 1665, 1640.

NMR(d$_6$-DMSO)δ: 0.82(t, J=6 Hz, 3H), 1.24(b-s, 8H), 1.46 and 1.52(two ds, J=6 Hz, 3H), 2.17(s, 6H), 2.18(t, J=6 Hz, 2H), 2.69(t, J=6 Hz, 2H), 3.37(s, 2H), 3.59 and 3.84(ABq, J=18 Hz, 2H), 4.14 and 4.35(ABq, J=13.5 Hz, 2H), 4.39(t, J=6 Hz, 2H), 5.03–5.19(m, 1H), 5.6–5.9(m, 1H), 6.23(s, 1H), 6.68–7.18(m, 3H), 8.86(d, J=9.0 Hz, 1H).

Elemental analysis: as $C_{27}H_{39}N_9O_6S_3.\frac{1}{2}H_2O$: Calcd: C, 46.94; H, 5.84; N, 18.24%, Found: C, 46.66; H, 5.82; N, 18.47%.

EXAMPLE 13

Preparation of 1-(n-octanoyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate:

The above mentioned compound was prepared in the same manner as in Example 6, using 1-iodoethyl n-octanoate.

IR(Nujol)cm$^{-1}$: 1780, 1750, 1670, 1640.

NMR(d$_6$-DMSO)δ: 0.84(t, J=6 Hz, 3H), 1.24(b-s, 10H), 1.47 and 1.52(two ds, J=6 Hz, 3H), 2.23(s, 6H), 2.30(t, J=6 Hz, 2H), 2.76(t, J=6Hz, 2H), 3.37(s, 2H), 3.71(b-s, 2H), 4.23 and 4.33(ABq, J=13.5 Hz, 2H), 4.40(t, J=6 Hz, 2H), 5.0–5.2(m, 1H), 5.4–5.9(m, 1H), 6.22(s, 1H), 6.7–7.7(m, 3H), 8.84(d, J=9 Hz, 1H).

Elemental analysis: as $C_{28}H_{41}N_9O_6S_3.\frac{1}{2}H_2O$: Calcd: C, 47.71; H, 6.00; N, 17.88%, Found: C, 47.65; H, 5.92; N, 17.94%.

EXAMPLE 14

Preparation of 1-(2-n-propylpentanoyloxy)ethyl 7β-[2-(2-aminothiazol-4-yl)acetamido]-3-[[[1-(2-dimethylaminoethyl)-1H-tetrazol-5-yl)thio]methyl]ceph-3-em-4-carboxylate:

The above mentioned compound was prepared in the same manner as in Example 6, using 1-iodoethyl 2-n-propylvalerate.

IR(Nujol)cm$^{-1}$: 1780, 1750, 1670.

NMR(d$_6$-DMSO)δ: 0.7–1.0(m, 6H), 1.0–1.8(m, 11H), 2.17(s, 6H), 2.69(t, J=6 Hz, 2H), 3.37(s, 2H), 3.57 and 3.84(ABq, J=18 Hz, 2H), 4.01 and 4.28 (ABq, J=13.5 Hz, 2H), 4.37(t, J=6 Hz, 2H), 4.95–5.15(m, 1H), 5.55–5.85(m, 1H), 6.23(s, 1H), 6.65–7.15(m, 3H), 8.87(d, J=9 Hz, 1H).

Elemental analysis: as $C_{28}H_{41}N_9O_6S_3.\frac{1}{2}H_2O$: Calcd: C, 47.71; H, 6.01; N, 17.88%, Found: C, 47.84; H, 6.13; N, 17.58%.

EXAMPLE 15

Preparation of 1-(n-decanoyloxy)ethyl 7β-[2-(2-aminothiazol-4-yl)acetamido]-3-[[[1-(2-dimethylaminoethyl)-1H-tetrazol]thio]methyl]ceph-3-em-4-carboxylate:

The above mentioned compound was prepared in the same manner as in Example 6, using 1-iodoethyl n-decanoate.

IR(Nujol)cm$^{-1}$: 1780, 1750, 1670.

NMR(d$_6$-DMSO)δ: 0.84(t, J=6 Hz, 3H), 1.23(b-s, 14 Hz), 1.39–1.50(two ds, J=6 Hz, 3H), 2.18(s, 6H), 2.33(t, J=6 Hz, 2H), 2.71(t, J=6 Hz, 2H), 3.37(s, 2H), 3.36 and 3.86(ABq, J=18 Hz, 2H), 4.16 and 4.33(ABq, J=13.5 Hz, 2H), 4.39(t, J=6 Hz, 2H), 5.02–5.08(m, 1H), 5.6–5.9(m, 1H), 6.23(s, 1H), 6.85–7.2(m, 3H), 8.95(d, J=9 Hz, 1H).

Elemental analysis: as $C_{30}H_{45}N_9O_6S_3$: Calcd: C, 49.77; H, 6.27; N, 17.41%; Found: C, 49.55; H, 6.27; N, 17.55%.

EXAMPLE 16

Preparation of 1-(n-hexanoyloxy)propyl 7β-[2-(2-aminothiazol-4-yl)acetamido]-3-[[[1-(2-dimethylaminoethyl)-1H-tetrazol-5-yl]thio]methyl]ceph-3-em-4-carboxylate:

The above mentioned compound was prepared in the same manner as of Example 6, using 1-iodopropyl n-hexanoate.

IR(Nujol)cm$^{-1}$: 1780, 1750, 1715, 1670, 1640.

NMR(d$_6$-DMSO)δ: 0.83(t, J=6 Hz, 3H), 0.91(t, J=6 Hz, 3H), 1.1–2.0(m, 8H), 2.27(t, J=6 Hz, 2H), 2.67(t, J=6 Hz, 2H), 3.36(s, 2H), 3.73(b-s, 2H), 4.14 and 4.32(ABq, J=13.5 Hz, 2H), 4.37(t, J=6 Hz, 2H), 5.0–5.20(m, 1H), 5.5–5.9(m, 1H), 6.21(s, 1H), 6.6–7.0(m, 3H), 8.84(d, J=9 Hz, 1H).

Elemental analysis: as $C_{27}H_{39}N_9O_6S_3$: Calcd: C, 47.56; H, 5.76; N, 18.49%, Found: C, 47.47; H, 5.55; N, 18.25%.

EXAMPLE 17

Preparation of 1-(n-hexanoyloxy)propyl 7β-[2-(2-aminothiazol-4-yl)acetamido]-3-[[[1-(2-dimethylaminoethyl)-1H-tetrazol-5-yl]thio]methyl]ceph-3-em-4-carboxylate.dihydrochloride:

The compound prepared in Example 16 was treated in the same way as Example 7 to give the above mentioned compound.

IR(Nujol)cm$^{-1}$: 1780, 1755, 1680.

NMR(d$_6$-DMSO)δ: 1.23(d, J=6 Hz, 3H), 1.39–2.47(m, 11H), 1.72(t, J=7 Hz, 2H), 3.37(s, 6H), 4.10(b-s, 2H), 4.36(t, J=6 Hz, 2H), 4.50 and 4.70(ABq, J=16 Hz, 2H), 5.25(t, J=6 Hz, 2H), 5.46(d, J=4.5 Hz, 1H), 6.00(d, J=4.5 Hz, 1H), 6.99(s, 1H), 7.10(q, J=4.5 Hz, 1H).

Elemental analysis: as $C_{27}H_{39}N_9O_6S_3.2HCl.2.5H_2O$: Calcd: C, 40.54; H, 5.81; N, 15.76%, Found: C, 40.71; H, 5.44; N, 15.92%.

EXAMPLE 18

Preparation of 2-n-butylhexanoyloxymethyl 7β-[2-(2-aminothiazol-4-yl)acetamido]-3-[[[1-(2-dimethylaminoethyl)-1H-tetrazol-5-yl]thio]methyl]ceph-3-em-4-carboxylate:

The above mentioned compound was prepared in the same manner as in Example 6, using iodomethyl 2-n-butylhexanoate.

IR(Nujol)cm$^{-1}$: 1780, 1750, 1720, 1665, 1640.

NMR(d$_6$-DMSO)δ: 0.84(t, J=6 Hz, 6H), 1.0–1.8 (m, 12H), 2.27(s, 6H), 2.81(t, J=6 Hz, 2H), 3.38(s, 2H), 3.73(b-s, 2H), 4.05 and 4.34 (ABq, J=13.5 Hz, 2H), 4.44(t, J=6 Hz, 2H), 5.10(d, J=4.5 Hz, 1H), 5.6–6.0(m, 3H), 6.23 (s, 1H), 6.83(b-s, 2H), 8.88(d, J=9 Hz, 1H).

Elemental analysis: as $C_{29}H_{43}N_9O_6S_2.\frac{1}{2}H_2O$: Calcd: C, 48.45; H, 6.17; N, 17.54%, Found: C, 48.41; H, 6.11; N, 17.21%.

EXAMPLE 19

Preparation of 2-n-butylhexanoyloxymethyl 7β-[2-(2-aminothiazol-4-yl)acetamido]-3-[[[1-(2-dimethylaminoethyl)-1H-tetrazol-5-yl]thio]methyl]ceph-3-em-4-carboxylate.dihydrochloride.

The compound prepared in Example 18 was treated in the same manner as Example 7 to give the above mentioned compound.

IR(Nujol)cm$^{-1}$: 1780, 1760, 1665.

NMR(d$_6$-DMSO)δ: 1.16(b-s, 6H), 1.60–2.32(b-s, 13H), 3.32(s, 6H), 4.00–4.62(m, 4H), 5.39(t, J=6 Hz, 2H), 5.50(d, J=4.5 Hz, 1H), 5.83(b-s, 2H), 5.98(d, J=4.5 Hz, 1H), 7.00(s, 1H).

Elemental analysis: as $C_{29}H_{43}N_9O_6S_3.2HCl.1.5H_2O$: Calcd: C, 43.01; H, 5.98; N, 15.56%, Found: C, 43.18; H, 6.49; N, 14.92.

EXAMPLE 20

Preparation of 2-n-hexyloctanoyloxymethyl 7β-[2-(2-aminothiazol-4-yl)acetamido]-3-[[[1-(2-dimethylaminoethyl)-1H-tetrazol-5-yl]thio]methyl]ceph-3-em-4-carboxylate:

The above mentioned compound was prepared in the same manner as in Example 6, using iodomethyl 2-n-hexyloctanoate.

IR(Nujol)cm$^{-1}$: 1780, 1760, 1675.

NMR(d$_6$-DMSO)δ: 0.84(t, J=6 Hz, 6H), 1.23(b-s, 20H), 2.21(s, 6H), 2.74(t, J=6 Hz, 2H), 3.37 (s, 2H), 3.73(b-s, 2H), 4.0–4.5(m, 1H), 4.17 and 4.27(ABq, J=13.5 Hz, 2H), 4.39(t, J=6 Hz, 2H), 5.10(d, J=4.5 Hz, 1H), 5.4–6.0(m, 3H), 6.21(s, 1H), 6.80(b-s, 2H), 8.86(d, J=9 Hz, 1H).

Elemental analysis: as $C_{33}H_{51}N_9O_6S_3$: Calcd: C, 51.74; H, 6.71; N, 16.46%, Found: C, 51.45; H, 6.84; N, 16.16%.

EXAMPLE 21

Preparation of 1-(2-ethylbutyryloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate:

The above mentioned compound was prepared in the same manner as in Example 6, using 1-iodoethyl 2-ethylbutyrate.

IR(Nujol)cm$^{-1}$: 1780, 1750, 1675.

NMR(d$_6$-DMSO)δ: 0.84(t, J=7 Hz, 6H), 1.2–1.75(m, 7H), 2.21(s, 6H), 0.69(t, J=6 Hz, 2H), 3.83 and 3.58(ABq, J=18 Hz, 2H), 4.00 and 4.17(ABq, J=13.5 Hz, 2H), 4.37(t, J=6 Hz, 2H), 5.08(d, J=4.5 Hz, 1H), 5.63–5.83(m, 1H), 6.25(s, 1H), 6.63–7.17(m, 3H), 8.89(d, J=8.9 Hz).

Elemental analysis: as $C_{26}H_{37}N_9O_6S_3$: Calcd: C, 46.75; H, 5.59; N, 18.88%, Found: C, 46.76; H, 5.49; N, 19.04%.

EXAMPLE 22

Preparation of 1-(2-ethylbutyryloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate.dihydrochloride:

The compound prepared in Example 21 was treated in the same manner as in Example 7 to give the above mentioned compound.

IR(Nujol)cm$^{-1}$: 1785, 1755, 1675

NMR(D$_2$O)δ: 1.05(t, J=7 Hz, 6H), 1.55–2.00(m, 7H), 2.55(t, J=6 Hz, 2H), 3.27(s, 6H), 3.85–4.25(m, 5H), 4.52(b-s, 2H), 5.15(t, J=6 Hz, 2H), 5.38(d, J=4.5 Hz, 1H), 5.88(d, J=4.5 Hz, 1H), 6.93(s, 1H), 7.17(q, J=6 Hz, 1H).

Elemental analysis: as $C_{26}H_{37}N_9O_6S_3.2HCl.1.5H_2O$: Calcd: C, 40.67; H, 5.51; N, 16.42; Cl, 9.24%, Found: C, 40.70; H, 5.89; N, 16.17; Cl, 9.74%.

EXAMPLE 23

Preparation of 1-(3-ethylpentanoyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate:

The above mentioned compound was prepared in the same manner as in Example 6, using 1-iodoethyl 3-ethylvalerate.

IR(Nujol)cm$^{-1}$: 1780, 1760, 1680.

NMR(d$_6$-DMSO)δ: 0.82(t, J=7 Hz, 6H), 1.1–1.8(m, 9H), 2.19(b-s, 8H), 2.70(t, J=6 Hz, 2H), 3.37(s, 2H), 3.58 and 3.84(ABq, J=18 Hz, 2H), 4.0–4.6 (m, 4H), 5.08(d, J=4.5 Hz, 1H), 5.6–5.9(m, 1H), 6.23(s, 1H), 6.6–7.2(m, 3H), 8.88(d, J=9 Hz, 1H)

Elemental analysis: as $C_{27}H_{39}N_9O_6S_3$: Calcd: C, 47.55; H, 5.78; N, 18.49%, Found: C, 47.08; H, 5.57; N, 18.10%.

EXAMPLE 24

Preparation of 1-(3-ethylpentanoyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate.dihydrochloride:

The compound prepared in Example 23 was treated in the same manner as Example 7 to give the above mentioned compound.

IR(Nujol)cm$^{-1}$: 1785, 1755, 1685.

NMR(D$_2$O)δ: 1.07(t, J=7 Hz, 6H), 1.45–2.17(m, 11H), 2.60(t, J=6 Hz, 2H), 3.30(s, 6H), 3.8–4.3(m, 5H), 4.65(b-s, 2H), 5.20(t, J=6 Hz, 2H), 5.45(d, J=4.5 Hz, 1H), 5.92(d, J=4.5 Hz, 1H), 7.00(s, 1H), 7.20(q, J=6 Hz, 1H).

Elemental analysis: as C$_{27}$H$_{39}$N$_9$O$_6$S$_3$.2HCl.2H$_2$O: Calcd: C, 41.01; H, 5.74; N, 15.94%, Found: C, 40.69; H, 5.92; N, 15.78%.

EXAMPLE 25

Preparation of 1-(3-methylpentanoyloxy)ethyl 7β-[2-(2-aminothiazol-4-yl)acetamido]-3-[[[1-(2-dimethylaminoethyl]-1H-tetrazol-5-yl]thio]methyl]ceph-3-em-4-carboxylate.dihydrochloride:

Step A: Preparation of 1-(3-methylpentanoyloxy)ethyl 7β-amino-3-[[[1-(2-dimethylaminoethyl)-1H-tetrazol-5-yl]thio]methyl]ceph-3-em-4-carboxylate.dihydrochloride:

To a solution of 4.22 g of 7β-amino-3-[[[1-(2-dimethylaminoethyl)-1H-tetrazol-5-yl]thio]methyl]ceph-3-em-4-carboxylic acid.dihydrochloride in 60 ml of dimethylformamide, 1.67 g of potassium acetate was added and the mixture was cooled to 0° C. with stirring. To the mixture, 5.0 g of 1-iodoethyl 3-methylvalerate was added dropwise, and the mixture was stirred at 0° C. for 5 minutes. The reaction mixture was then poured into a mixture of 60 ml of dichloromethane and 60 ml of 0.1 NHCl, and the aqueous layer was separated. The aqueous layer was adjusted to pH 6.0 with a saturated aqueous solution of sodium hydrogencarbonate and extracted with dichloromethane. The organic layer was admixed with water and adjusted to pH 2.0 with 4N HCl. The aqueous layer was separated and dichloromethane was removed from the aqueous layer under reduced pressure. The aqueous layer was lyophilized to give 2.83 g of the titled compound.

IR(Nujol)cm$^{-1}$: 1780, 1750, 1670.

Step B: To a mixture of 30 ml of water and 30 ml of dichloromethane was added 1.8 g of the compound prepared in the above step A. While the mixture was stirred, 0.55 g of sodium hydrogencarbonate was added. The organic layer was separated and dried over anhydrous calcium chloride. After the calcium chloride was filtered off, a solution of 0.60 g of (2-aminothiazol-4-yl)acetic acid.hydrochloride and 0.62 g of dicyclohexylcarbodiimide in 20 ml of dimethylformamide was added to the organic layer and the mixture was stirred at room temperature.

After the precipitates were removed by filtration, 150 ml of ethyl acetate and 100 ml of ice-cooled water were added to the filtrate. The organic layer was separated and washed with water and a saturated aqueous solution of sodium chloride, dried over anhydrous magnesium sulfate. After the magnesium sulfate was filtered off, the filtrate was condensed to 10 ml under reduced pressure. To the residual solution, was added anhydrous etheral hydrogen chloride. The precipitated white powdery product (0.35 g) was collected by filtration.

The NMR, IR spectra were in agreement with those of the product obtained in Example 11.

EXAMPLE 26

Preparation of 1-(3-methylpentanoyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate.dihydrochloride:

To a mixture of 15 ml of water and 15 ml of dichloromethane, was added 1.2 g of 1-(3-methylpentanoyloxy)ethyl 7β-amino-3-[[[1-(2-dimethylaminoethyl)-1H-tetrazol-5-yl]thio]methyl]ceph-3-em-4-carboxylate.dihydrochloride, followed by 0.30 g of sodium hydrogencarbonate. After the mixture was stirred, the organic layer was separated, and dried over anhydrous calcium chloride. After the solvent was removed under reduced pressure, the residue was dissolved in 15 ml of dichloromethane and the solution was cooled to −25° C. To this solution, was added a solution of 0.5 g of ω-chloroacetoacetyl chloride in 2.0 ml of dichloromethane. The mixture was stirred at −20°–−15° C. for 20 minutes. A solution of 0.76 g of thiourea in 5 ml of dimethylacetamide was added to the mixture, which was then stirred at room temperature for 3 hours. Water was added to the reaction mixture and the aqueous layer was separated, adjusted to pH 6.0 and extracted with dichloromethane. Water was added to the organic layer, which was then adjusted to pH 1.5 with 2N-HCl. The aqueous layer was separated and dichloromethane was removed from it under reduced pressure. The aqueous layer was subjected to the column chromatography on Amberlite XAD-II (produced by Rhom & Haas, USA, insoluble cross-linked polystyrol in bead form) with 120 ml of 0.01N HCl followed by 10% acetonitrile-0.01N HCl as eluents. The eluate was lyophilized to give 0.46 g of white powder. The NMR and IR spectra were in agreement with those of product in Example 11.

EXAMPLE 27

Preparation of 1-(2-ethylbutylyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate.

(a) Preparation of 1-(2-ethylbutyloxy)ethyl 7β-[2-(2-aminothiazol-4-yl)acetamido]-3-acetoacetoxymethyl-ceph-3-em-4-carboxylate.

In 30 ml of N,N-dimethyl formamide, 4.76 g of sodium 7β-[2-(2-aminothiazol-4-yl)acetamido]-3-acetoacetoxymethyl-ceph-3-em-4 carboxylate was dissolved. After the solution was cooled to −5° C., 5.0 g of 1-iodoethyl 2-ethylbutyrate was added dropwise under stirring and the stirring was maintained for 5 min. thereafter. Subsequently, the resulting crude product was treated in the same way as in Example 6 to yield 3.2 g of the titled product (a).

IR(KBr)cm$^{-1}$: 1780, 1745, 1680.

NMR(d$_6$-DMSO)δ: 0.84(t, J=7 Hz, 6H), 1.2–1.75(m, 7H), 2.10(s, 3H), 3.50(b-s, 2H), 3.60 and 3.85 (ABq, J=18.5 Hz, 2H), 4.03 and 4.20(ABq, J=13.5 Hz), 5.01(d, J=4.5 Hz, 1H), 5.6–5.8(m, 1H), 6.25(s, 1H), 6.6–7.2(m, 3H), 8.89(d, J=9 Hz, 1H).

(b) Preparation of 1-(2-ethylbutylyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate.

In 30 ml of acetone, 2.3 g of the compound obtained in the foregoing step (a) was dissolved. To this solution were added 10 ml of aqueous solution of 0.9 g of 1-(2-dimethylamino-ethyl)-5-mercapto-1H-tetrazole and 0.8 g of sodium bicarbonate and then warmed up to 40° C. under stirring for 1 hour. Thereafter, the reactant liquid was poured into a mixture of ethyl acetate (150 ml) and ice water (50 ml) and the organic layer was separated. The organic layer was washed successively with ice water and saturated aqueous solution of sodium chloride and dried over anhydrous magnesium sulfate. After magnesium sulfate was removed by filtration the solvent was removed in vacuo. The residue was recovered and was dissolved in acetone and insolubles were filtered off. To the filtrate was added isopropyl ether until powdery precipitates were deposited. The precipitates were recovered as white powdery product. The yield was 0.12 g.

NMR and IR spectrums of the power agreed with those of the specimen obtained in Example 21.

EXAMPLE 28

335 g of the compound prepared in Example 13, 70.5 g of hydroxypropylcellulose and 70.5 g of carboxymethylcellulose were homogeneously mixed. The mixture was packed in capsules in an amount of 249 mg per capsule (125 mg in terms of non-ester form of the compound).

EXAMPLE 29

378 g of the compound prepared in Example 19, 70 g of starch and 6 g of hydroxypropylcellulose were homogeneously mixed. The mixture was pressed into tablets in such an amount that 227 mg of the mixture was pressed into a tablet (125 mg in terms of non-ester form of the compound).

EXAMPLE 30

335 g of the compound prepared in Example 14, 357 g of tartaric acid and 26 g of starch were uniformly mixed and wet-granulated in accordance with a conventional method. The granules were combined with 18 g of microcrystalline cellulose and 4 g of magnesium stearate and pressed into tablets in such an amount that each tablet is made of 359 mg of the mixture (125 mg in terms of non-ester form of the compound).

EXAMPLE 31

335 g of the compound prepared in Example 14, 357 g of powdery tartaric acid, 37 g of microcrystalline cellulose and 2 g of magnesium stearate were uniformly mixed, and the mixture was pressed into slugg with a slugg presser. The slugg was granulated and combined with a mixture of 3.5 g of magnesium stearate and 16.5 g of microcrystalline cellulose as a lubricant.

The mixture was pressed into tablets in such an amount that each tablet is made of 364 mg of the mixture (125 mg in terms of non-ester form of the compound).

Bioavailability Test

Test compounds: compounds obtained in examples 6, 8, 10, 13, 14, 16, 21, 23 and compound for control: pivaloyloxymethyl 7β-[2-(2-aminothiazol-4-yl)acetamido]-3-[[[1-(2-dimethylaminoethyl)-1H-tetrazol-5-yl]thio]methyl]-ceph-3-em-4-carboxylate (This will be referred to simply "compound A" hereinafter).

Male SLC-ICR mice (4 weeks old) were starved but under free access to drinking water for 16–18 hr. period to the experiments. The test compound was administered orally by intubation as an aqueous solution with 2.5 equimolar of tartaric acid at a dose of 100 mg/kg as non-ester form of the Compound I, to a group of four mice. The blood was taken from the inferior vena cava at 0.25, 0.5, 1 and 2 hours after dosing. The concentration of the non-ester form of the Compound I in the plasma was measured by the cylinder-plate method using *Proteus mirabilis* ATCC 21100 as an assay organism.

Control test: an aqueous solution of non-ester form of the Compound I in an amount of 10 ml water/Kg mouse body weight, was subcutaneously applied and AUC was calculated in the same manner as above.

The Bioavailability defined in the following formula is shown in the Table 1.

$$\text{Bioavailability (\%)} = \frac{AUC \text{ (oral administration)}}{AUC \text{ (subcutaneous administration)}} \times 100$$

TABLE 1

| Compound tested | AUC (μg · hr/ml) | Bioavailability (%) |
|---|---|---|
| Example 6 | 26.2 | 67.5 |
| Example 8 | 20.5 | 52.8 |
| Example 10 | 36.2 | 93.2 |
| Example 13 | 23.5 | 60.6 |
| Example 14 | 25.6 | 66.0 |
| Example 16 | 25.2 | 65.0 |
| Example 21 | 38.8 | 100.0 |
| Example 23 | 30.3 | 78.2 |
| Compound A | 16.2 | 41.8 |
| (control) non-ester form of Compound I | 38.8 | 100 |

Area under plasma-concentration curve (AUC) for 0 to 2 hr. after administration was calculated by the trapezoidal rule.

We claim:

1. A compound of the formula:

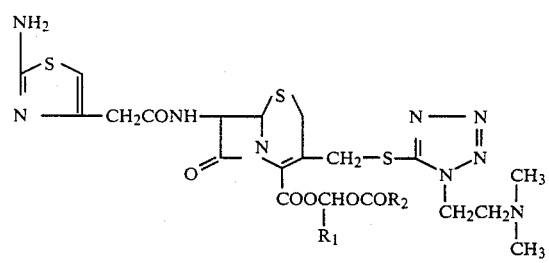

wherein $R_1$ is methyl or ethyl; and $R_2$ is a straight-chain or branched alkyl group of 5 to 7 carbon atoms or its pharmaceutically acceptable salt.

2. A compound according to claim 1, wherein $R_2$ is pentyl, 2-methylbutyl, heptyl or 1-propylbutyl.

3. A compound according to claim 1, wherein the pharmaceutically acceptable salt is hydrochloride.

4. A compound according to claim 1, the compound of the formula being 1-(3-methylpentanoyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate.

5. A compound according to claim 1, the compound of the formula being 1-(3-ethylpentanoyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate.

6. A compound accordint to claim 1, the compound of the formula being 1-(2-ethylbutyryloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate.

7. A compound according to claim 1, the compound of the formula being 1-(n-hexanoyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate.

8. A compound according to claim 1, the compound of the formula being 1-(4-methylpentanoyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate.

9. A compound according to claim 1, the compound of the formula being 1-(n-octanoyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate.

10. A compound according to claim 1, the compound of the formula being 1-(2-n-propylpentanoyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate.

11. A compound according to claim 1, the compound of the formula being 1-(n-hexanoyloxy)propyl 7β-[2-(2-aminothiazol-4-yl)acetamido[-3-[[[1-(2-dimethylaminoethyl)-1H-tetrazol-5-yl]thio]methyl]ceph-3-em-4-carboxylate.

12. A pharmaceutical composition comprising a compound of the formula:

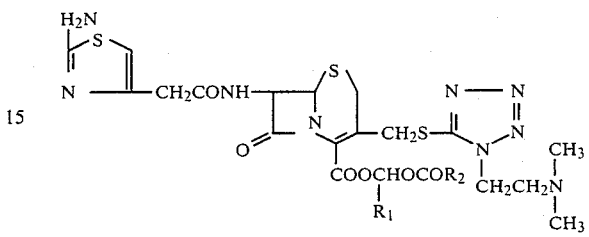

wherein $R_1$ is methyl or ethyl; and $R_2$ is a straight-chain or branched alkyl group of 5 to 7 carbon atoms, or its pharmaceutically acceptable salt as an effective ingredient.

* * * * *